US010966850B2

(12) United States Patent
Irwin et al.

(10) Patent No.: US 10,966,850 B2
(45) Date of Patent: Apr. 6, 2021

(54) IMPLANTABLE MEDICAL DEVICE CONSTRAINT AND DEPLOYMENT APPARATUS

(71) Applicant: W. L. Gore & Associates, Inc., Newark, DE (US)

(72) Inventors: Craig W. Irwin, Parks, AZ (US); James D. Silverman, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 109 days.

(21) Appl. No.: 14/639,699

(22) Filed: Mar. 5, 2015

(65) Prior Publication Data

US 2015/0250630 A1    Sep. 10, 2015

Related U.S. Application Data

(60) Provisional application No. 61/949,100, filed on Mar. 6, 2014.

(51) Int. Cl.
*A61F 2/962* (2013.01)
*A61F 2/95* (2013.01)
(Continued)

(52) U.S. Cl.
CPC .......... *A61F 2/95* (2013.01); *A61B 17/12022* (2013.01); *A61F 2/962* (2013.01);
(Continued)

(58) Field of Classification Search
CPC .. A61F 2/95; A61F 2/962; A61F 2/966; A61F 2/2427; A61F 2/2436; A61F 2/97; A61F 2002/9517
See application file for complete search history.

(56) References Cited

U.S. PATENT DOCUMENTS

| 5,445,646 A | * | 8/1995 | Euteneuer | A61F 2/95 |
| | | | | 604/103.02 |
| 5,571,135 A | * | 11/1996 | Fraser | A61F 2/95 |
| | | | | 606/198 |

(Continued)

FOREIGN PATENT DOCUMENTS

| EP | 2175813 A1 | 4/2010 |
| EP | 2 352 464 | 8/2011 |
| EP | 2491894 A1 | 8/2012 |
| JP | 2002-518086 A | 6/2002 |
| JP | 2002-537026 A | 11/2002 |

(Continued)

OTHER PUBLICATIONS

Annex to Form PCT/ISA/206 Communication Relating to the Results of the Partial International Search, PCT/US2015/019271 dated May 29, 2015 corresponding to U.S. Appl. No. 14/639,699, 4 pages.

(Continued)

*Primary Examiner* — Ryan J. Severson

(57) ABSTRACT

An implantable medical device deployment system is disclosed that employs both a sheath element and a constraint member to protect implantable medical devices during delivery in a body while providing simple, accurate, and reliable device deployment. The delivery system is configured so that loading and deployment forces are not directly related to device diameter, length, or design, thus allowing a more universal delivery system across various delivered device configurations and product lines. The deployment system can provide numerous benefits, include better protection for drug-coated implantable devices.

28 Claims, 8 Drawing Sheets

(51) Int. Cl.
*A61B 17/12* (2006.01)
*A61F 2/966* (2013.01)

(52) U.S. Cl.
CPC .... *A61F 2/966* (2013.01); *A61B 2017/12054* (2013.01); *A61F 2/9517* (2020.05); *A61F 2/9522* (2020.05); *A61F 2250/0067* (2013.01); *Y10T 29/49872* (2015.01)

(56) References Cited

U.S. PATENT DOCUMENTS

| | | | |
|---|---|---|---|
| 5,647,857 A * | 7/1997 | Anderson | A61F 2/958 604/160 |
| 5,662,703 A * | 9/1997 | Yurek | A61F 2/95 606/194 |
| 5,989,280 A * | 11/1999 | Euteneuer | A61F 2/95 623/1.1 |
| 6,059,813 A * | 5/2000 | Vrba | A61F 2/01 606/198 |
| 6,224,627 B1 | 5/2001 | Armstrong et al. | |
| 6,254,628 B1 * | 7/2001 | Wallace | A61B 17/12118 623/1.12 |
| 6,315,792 B1 | 11/2001 | Armstrong et al. | |
| 6,383,171 B1 * | 5/2002 | Gifford | A61F 2/013 604/508 |
| 6,398,758 B1 | 6/2002 | Jacobsen et al. | |
| 6,544,278 B1 * | 4/2003 | Vrba | A61F 2/01 606/192 |
| 7,201,770 B2 * | 4/2007 | Johnson | A61F 2/958 623/1.12 |
| 7,285,130 B2 | 10/2007 | Austin | |
| 7,632,296 B2 * | 12/2009 | Malewicz | A61F 2/966 623/1.11 |
| 7,794,488 B2 * | 9/2010 | Vrba | A61F 2/966 623/1.11 |
| 8,016,872 B2 * | 9/2011 | Parker | A61F 2/95 623/1.11 |
| 8,435,282 B2 * | 5/2013 | Silverman | A61F 2/962 623/1.15 |
| 8,641,752 B1 * | 2/2014 | Holm | A61F 2/97 623/1.12 |
| 8,764,816 B2 * | 7/2014 | Koss | A61F 2/966 623/1.23 |
| 8,801,774 B2 * | 8/2014 | Silverman | A61F 2/962 623/1.15 |
| 8,845,712 B2 | 9/2014 | Irwin et al. | |
| 8,936,634 B2 * | 1/2015 | Irwin | A61F 2/88 623/1.15 |
| 9,114,037 B2 * | 8/2015 | Silverman | A61F 2/962 |
| 9,526,641 B2 * | 12/2016 | Irwin | A61F 2/01 |
| 10,213,329 B2 * | 2/2019 | Cully | A61F 2/958 |
| 2001/0044595 A1 * | 11/2001 | Reydel | A61F 2/95 604/98.02 |
| 2001/0056295 A1 * | 12/2001 | Solem | A61F 2/97 623/1.11 |
| 2002/0099431 A1 * | 7/2002 | Armstrong | A61F 2/97 623/1.11 |
| 2002/0138129 A1 * | 9/2002 | Armstrong | A61F 2/86 623/1.11 |
| 2003/0004561 A1 | 1/2003 | Bigus | |
| 2003/0105508 A1 * | 6/2003 | Johnson | A61F 2/958 623/1.11 |
| 2003/0135258 A1 * | 7/2003 | Andreas | A61F 2/95 623/1.11 |
| 2003/0199966 A1 * | 10/2003 | Shiu | A61F 2/95 623/1.12 |
| 2003/0212410 A1 * | 11/2003 | Stenzel | A61F 2/958 606/108 |
| 2005/0165352 A1 * | 7/2005 | Henry | A61F 2/97 604/108 |
| 2005/0240254 A1 * | 10/2005 | Austin | A61F 2/95 623/1.11 |
| 2006/0015171 A1 * | 1/2006 | Armstrong | A61B 17/12109 623/1.12 |
| 2006/0030923 A1 * | 2/2006 | Gunderson | A61F 2/966 623/1.11 |
| 2006/0030924 A1 * | 2/2006 | Van Der Leest | A61F 2/97 623/1.11 |
| 2006/0041302 A1 * | 2/2006 | Malewicz | A61F 2/966 623/1.11 |
| 2006/0089627 A1 * | 4/2006 | Burnett | A61B 17/12099 606/1 |
| 2006/0122685 A1 * | 6/2006 | Bonsignore | A61F 2/07 623/1.13 |
| 2006/0184226 A1 * | 8/2006 | Austin | A61F 2/95 623/1.11 |
| 2006/0200221 A1 * | 9/2006 | Malewicz | A61F 2/966 623/1.11 |
| 2007/0060999 A1 * | 3/2007 | Randall | A61F 2/95 623/1.11 |
| 2007/0191925 A1 | 8/2007 | Dorn | |
| 2007/0208350 A1 * | 9/2007 | Gunderson | A61F 2/95 606/108 |
| 2007/0244540 A1 * | 10/2007 | Pryor | A61F 2/97 623/1.11 |
| 2008/0140003 A1 * | 6/2008 | Bei | A61F 2/95 604/103.05 |
| 2008/0167705 A1 * | 7/2008 | Agnew | A61F 2/97 623/1.12 |
| 2008/0255580 A1 * | 10/2008 | Hoffman | A61F 2/95 606/108 |
| 2008/0281398 A1 | 11/2008 | Koss et al. | |
| 2009/0018501 A1 * | 1/2009 | Yribarren | A61M 25/0119 604/103.01 |
| 2009/0099638 A1 | 4/2009 | Grewe | |
| 2009/0182411 A1 * | 7/2009 | Irwin | A61F 2/966 623/1.12 |
| 2009/0192584 A1 * | 7/2009 | Gerdts | A61F 2/95 623/1.11 |
| 2009/0254063 A1 * | 10/2009 | Oepen | A61M 25/1006 604/509 |
| 2009/0270969 A1 * | 10/2009 | Fargahi | A61F 2/962 623/1.11 |
| 2009/0299449 A1 * | 12/2009 | Styrc | A61F 2/966 623/1.11 |
| 2009/0326449 A1 | 12/2009 | Wang et al. | |
| 2010/0004606 A1 * | 1/2010 | Hansen | A61F 2/966 604/264 |
| 2010/0036472 A1 * | 2/2010 | Papp | A61F 2/95 623/1.11 |
| 2010/0069852 A1 * | 3/2010 | Kelley | A61F 2/2436 604/264 |
| 2010/0168835 A1 * | 7/2010 | Dorn | A61F 2/95 623/1.11 |
| 2011/0009943 A1 * | 1/2011 | Paul | A61B 17/12109 623/1.11 |
| 2011/0015716 A1 * | 1/2011 | Silverman | A61F 2/82 623/1.2 |
| 2011/0034987 A1 * | 2/2011 | Kennedy | A61F 2/95 623/1.11 |
| 2011/0118817 A1 * | 5/2011 | Gunderson | A61F 2/95 623/1.12 |
| 2011/0137402 A1 | 6/2011 | Dorn | |
| 2011/0166637 A1 * | 7/2011 | Irwin | A61F 2/88 623/1.13 |
| 2012/0016454 A1 * | 1/2012 | Jantzen | A61F 2/966 623/1.11 |
| 2012/0059448 A1 * | 3/2012 | Parker | A61F 2/95 623/1.11 |
| 2012/0130474 A1 * | 5/2012 | Buckley | A61F 2/97 623/1.12 |
| 2012/0165915 A1 * | 6/2012 | Melsheimer | A61F 2/82 623/1.11 |
| 2013/0006220 A1 * | 1/2013 | Yribarren | A61M 25/1006 604/509 |
| 2013/0150949 A1 * | 6/2013 | Silverman | A61F 2/88 623/1.15 |

(56) References Cited

U.S. PATENT DOCUMENTS

| | | | |
|---|---|---|---|
| 2013/0204345 A1* | 8/2013 | Cully | A61F 2/966 623/1.12 |
| 2013/0211493 A1* | 8/2013 | Wubbeling | A61F 2/95 623/1.11 |
| 2013/0238080 A1* | 9/2013 | Silverman | A61F 2/966 623/1.12 |
| 2013/0245742 A1 | 9/2013 | Norris | |
| 2013/0296877 A1* | 11/2013 | Irwin | A61B 17/3468 606/108 |
| 2013/0340233 A1* | 12/2013 | Tollner | A61F 2/966 29/428 |
| 2014/0081376 A1* | 3/2014 | Burkart | A61F 2/97 623/1.12 |
| 2014/0358156 A1* | 12/2014 | Argentine | A61F 2/966 606/108 |
| 2015/0134043 A1* | 5/2015 | Irwin | A61F 2/88 623/1.13 |
| 2015/0250630 A1* | 9/2015 | Irwin | A61B 17/12022 606/108 |
| 2019/0247210 A1* | 8/2019 | Cully | A61F 2/958 |

FOREIGN PATENT DOCUMENTS

| | | |
|---|---|---|
| JP | 2007-534441 A | 11/2007 |
| JP | 2010-526583 A | 8/2010 |
| WO | WO-1999065420 A1 | 12/1999 |
| WO | WO-2000048645 A2 | 8/2000 |
| WO | WO-2005107644 A1 | 11/2005 |
| WO | 2008/034793 A1 | 3/2008 |
| WO | WO-2008137177 A2 | 11/2008 |
| WO | 2009/012061 A1 | 1/2009 |
| WO | WO-2010063794 A1 | 6/2010 |
| WO | 2013/025470 | 2/2013 |

OTHER PUBLICATIONS

International Preliminary Report on Patentability received for PCT Patent Application No. PCT/US2015/019271, dated Sep. 15, 2016, 10 pages.

International Search Report and Written Opinion received for PCT Patent Application No. PCT/US15/019271, dated Oct. 19, 2015, 16 pages.

* cited by examiner

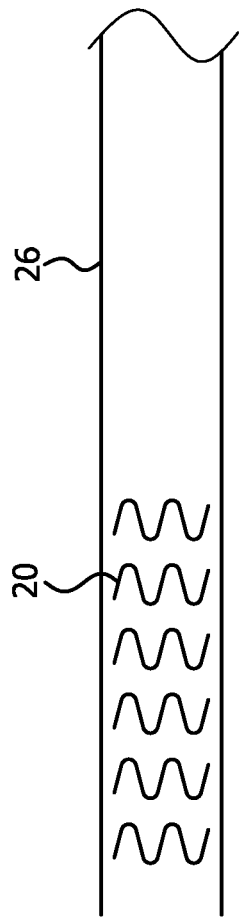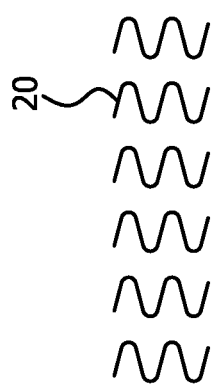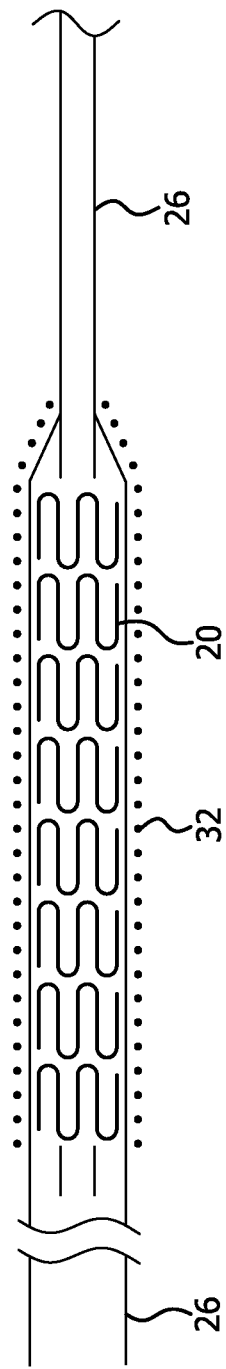

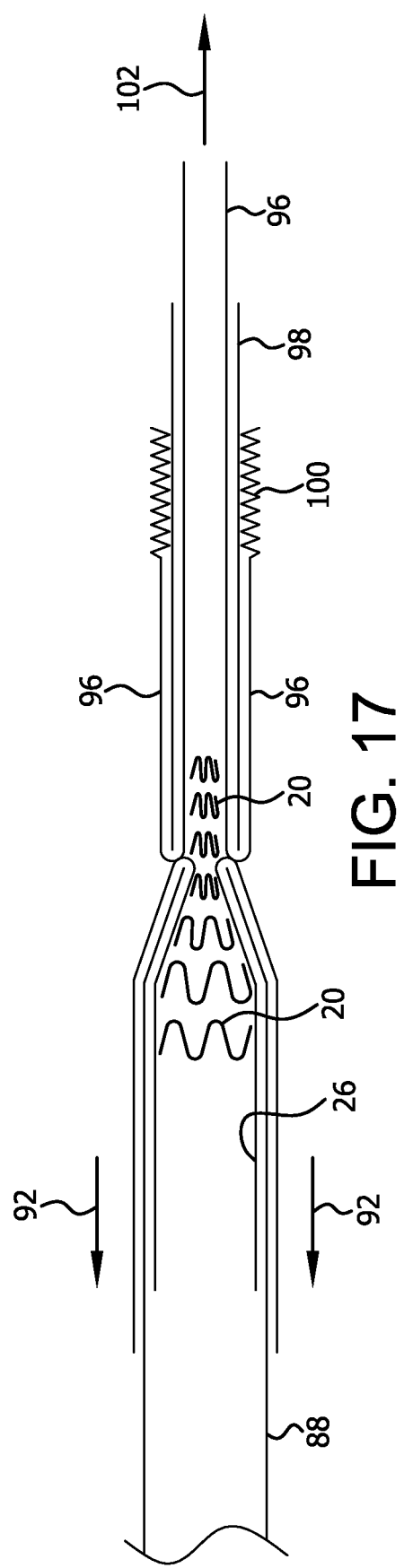
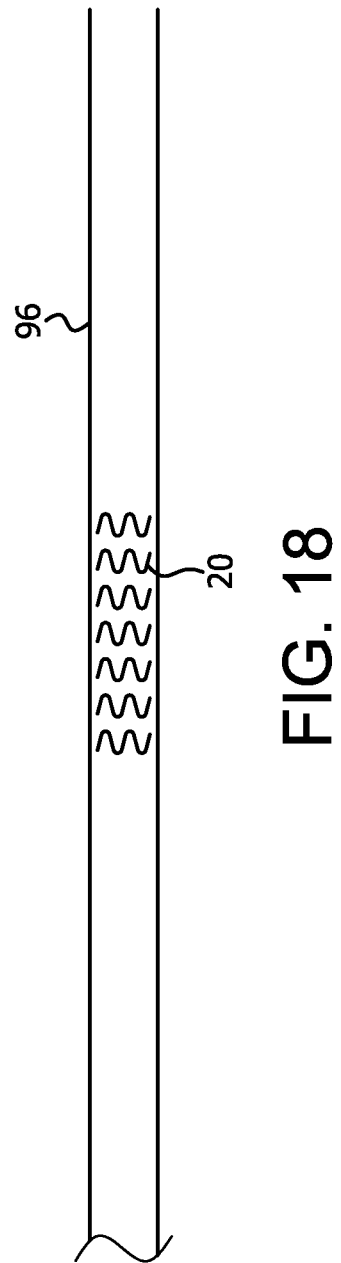
FIG. 17
FIG. 18

IMPLANTABLE MEDICAL DEVICE CONSTRAINT AND DEPLOYMENT APPARATUS

BACKGROUND OF THE INVENTION

Field of the Invention

The invention relates to apparatus and methods for the delivery and deployment of implantable medical devices.

Discussion of the Related Art

With the growing proliferation of sophisticated implantable medical devices and more advanced treatment apparatus, and particularly medical devices and treatments that are delivered and deployed through minimally invasive procedures such as stents, stent-grafts, balloons, filters, occluders, and the like, there has been a growing interest in finding improved devices and methods to effectively constrain, deliver, and/or deploy such devices and treatment apparatus.

Examples of previous devices and methods for delivering and deploying such devices include the use of everting sleeves to constrain the implantable device and then deploy the devices in a controlled manner in situ, such as the devices described in U.S. Pat. No. 7,285,130 to Austin, US Application 2008-0281398 to Koss et al., and PCT Application WO13025470 to Cully et al. The use of everting sleeves as described in these references has many advantages, but there are limitations on length, geometry, tensile strength, and other properties of the devices that can be effectively mounted in and deployed from many of these sleeves. Additionally, prior everting sleeves deployment apparatus have been challenged to balance adequate constraint of implantable devices prior to deployment against accurate and easy deployment of the implantable devices in the desired location in the body.

Another prior constraint and delivery apparatus that has been technically and commercially successful is described in U.S. Pat. No. 6,315,792 to Armstrong et al. This apparatus employs a knitted fiber cover that constrains the implantable device prior to deployment, which is then removed to allow the device to deploy in the desired location in the body. While this apparatus works very well, it also has limitations on the size and types of implantable devices that it can effectively constrain and deploy. One concern with this and other fiber constraints is that fibrous covers may not smoothly mount and/or deploy from certain device geometries or features (e.g., fibers may catch of barbs or other features on the implantable device).

Even more recent interest in providing implantable devices and treatment apparatus that are covered with drugs or other bioactive agent has further increased the challenge of effectively constraining and delivering such devices. The act of pulling a drug coated device through a funnel into a constraining apparatus runs a serious risk that bioactive agent may be removed or displaced during the loading and mounting process, which could compromise the effectiveness of the device once deployed. Similarly, interaction between the constraint and the implantable device during deployment also creates a risk that the bioactive agent may not remain properly applied to the device once fully deployed.

SUMMARY OF THE INVENTION

The present invention provides a scalable delivery system that protects medical devices during delivery in a body while providing simple, accurate, and reliable device deployment. The delivery system is configured so that loading and deployment forces are not directly related to device diameter, length, or design, thus providing a more useful delivery system that can be employed across various delivered device configurations and product lines.

Among the advantages of the delivery system of the present invention are: more predictable deployment forces that facilitate smoother and more predictable device delivery (e.g., by reducing adverse interaction between the implantable device and the constraint, there is less risk of snagging and catheter displacement); ability to deploy devices with irregular features (e.g., scallops, barbs, anchors, apices, and other features that may interfere with smooth operation of deployment apparatus); ability to create devices with smaller device delivery profiles; ability to contain delivery lines within a sheath so as to reduce or eliminate "bow-stringing" of the line during deployment; and ability to protect an implantable device from shear forces during manufacture and delivery, which is particularly useful to shield various coatings (e.g., drugs or other bio-active materials) applied to the device from damage or premature release.

A further benefit of the present invention is that it imparts minimal stress to the delivered device. In the present invention the delivered device is encapsulated prior to loading and remains encapsulated until deployment. For drug delivery devices, this reduces drug loss and particulation. This may also eliminate contact between device and tooling during device mounting and isolates the device from surface shear during loading and deployment. The present invention also can eliminate tensioning of device during loading so as to allow for lower implantable device mass and lower profile.

In one embodiment of the present invention, a deployment system for an implantable medical device is provided that comprises an expandable medical device having a larger deployed diameter and a smaller compacted diameter for delivery; a sheath surrounding the compacted medical device, the sheath everted back over itself, wherein an outer portion of the sheath surrounds an inner portion of the sheath; and a filamentary constraining member, located between the inner and outer portions of the sheath, wherein the medical device is deployed to the larger diameter by the application of simultaneous actuation forces to the sheath and the filamentary constraining member.

In another embodiment of the present invention, a method for loading an implantable device on a deployment system is provided that comprises: providing an implantable device; placing the implantable device within a sheath element that includes a segment extending beyond the implantable device; providing a funnel and a constraining element; applying tension on the segment of the sheath element to pull the sheath element and the implantable device through the funnel so as to compact the implantable device within the sheath element and into the constraining element so that the implantable device is constrained in a compacted state; wherein the sheath element and constraining element are configured to be removed to deploy the implantable device in use.

In a further embodiment of the present invention directed to device deployment, a medical device deployment system is provided that comprises: a first sheath and a second sheath, wherein each of the first and second sheaths is non-proportionally actuated by the application of tension to tensile members connected to each of the first and second sheaths, wherein on deployment by the application of a single input force, the input force is variably distributed between said tensile members.

In an additional embodiment of the present invention, a medical device deployment system is provided that comprises: two or more pulleys that engage through a rotating planetary rolling element, wherein each of the pulleys is configured to accumulate a deployment line, wherein the deployment lines actuate deployment of the medical device.

BRIEF DESCRIPTION OF THE DRAWINGS

The accompanying drawings are included to provide a further understanding of the invention and are incorporated in and constitute a part of this specification, illustrate embodiments of the invention, and together with the description serve to explain the principles of the invention.

FIG. 2 is a side view of an implantable device prior to constraint into the delivery and deployment apparatus of the present invention.

FIG. 3 is a side view of a traction tube sheath element of the present invention surrounding the implantable device shown in FIG. 2.

FIG. 6 is a side view of the sheath element, implantable device, and constraining member combination created in the process illustrated by FIG. 4 or FIG. 5 shown prior to mounting on a delivery catheter.

FIG. 17 is a side view, shown partially in cross-section, of the implantable device, sheath element, and transfer funnel combination shown in FIG. 15 and the second sheath element and transfer tube combination shown in FIG. 16 arranged in abutted orientation with each other and with the implantable device shown partially transferred from the transfer funnel to the transfer tube.

FIG. 18 is a side view, shown partially in cross-section, of the implantable device mounted within the second sheath following the transfer process illustrated in FIG. 17.

DETAILED DESCRIPTION OF THE ILLUSTRATED EMBODIMENTS

The present invention provides improved apparatus to constrain, deliver, and/or deploy a medical device. The invention may be used in conjunction with a wide variety of devices that may be temporarily or permanently deployed in a patient, including without limitation stents, stent-grafts, balloons, filters, traps, occluders, devices for delivering drugs or other therapeutic substances or treatments, and the like. As such, the terms "medical device" and "implantable device" in the present application are intended to be broadly construed to encompass any device that is temporarily or permanently placed in a body.

The apparatus of the present invention may be employed to deliver self-expanding devices, devices that are expandable by balloons or other means, self-expanding/expandable hybrid devices, and devices that are not intended to change dimensions in situ.

Particular embodiments of the present invention are described below by way of illustration. It should be understood by one of skill in the art that the present inventors do not intend to limit the scope of the present invention to these particular embodiments.

Figure 1:
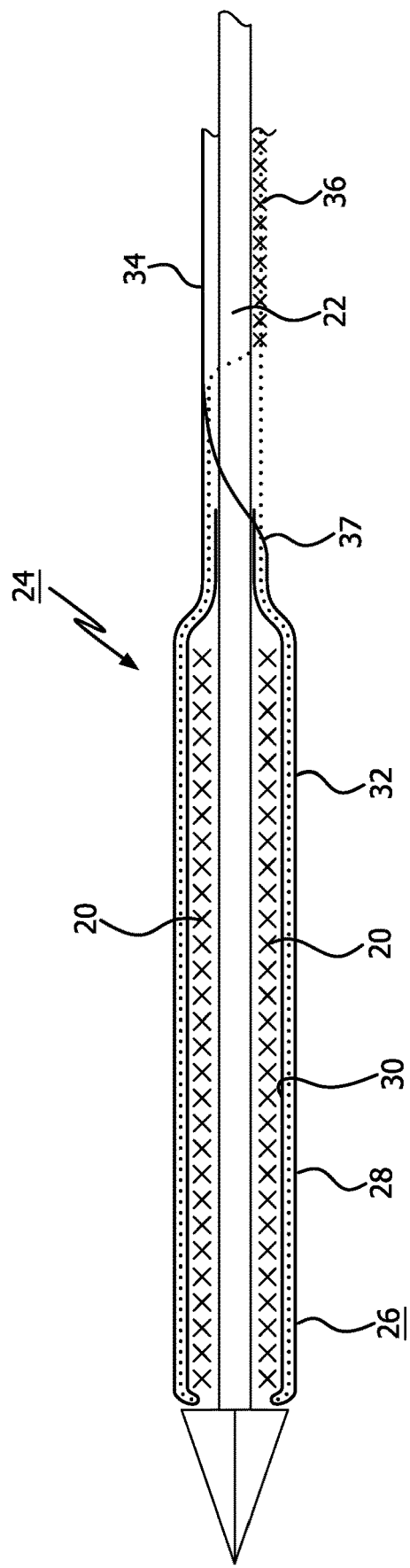
FIG. 1 is a side cross-section view of an implantable device constrained in a delivery and deployment apparatus of the present invention.

FIG. 1 shows an implantable device 20, in this case a stent or stent-graft, mounted on a catheter 22 and constrained in a deployment apparatus 24 of the present invention. The deployment apparatus 24 comprises an everted traction tube sheath element 26 having an outer layer 28 and an inner layer 30. Contained within the outer layer 28 and the inner layer 30 of the sheath element 26 is a constraining member 32. The deployment apparatus 24 includes a first deployment line 34 operatively coupled to actuate the sheath 26 and a second deployment line 36 operatively coupled to actuate the constraining member 32.

As is explained in greater detail below, the sheath element 26 is constructed from a thin, flexible material that is adapted to surround and protect the implantable device. The flexible material should have sufficient longitudinal tensile strength so that it can serve as a traction tube to help pull the implantable device 20 through compaction apparatus and into the constraining member 32 during the manufacturing process. Preferably the flexible material should also have sufficient coverage and structural integrity to protect any bioactive coating or other surface treatment on the implantable device until the device is ultimately deployed in vivo. It may further be desirable for the flexible sheath to be constructed from a lubricious material that can aid in the manufacturing process described below.

The sheath element 26 is not required to provide any significant constraint to the implantable device 20 as that function, if required, may be primarily provided by the constraining member 32. As such, the sheath element 26 may be constructed from very thin and flexible material that exhibits some degree of radial compliance. In fact, it may be desirable for the sheath element 26 undergo necking when under longitudinal tension so as to aid in the compaction process during manufacturing.

The flexible material of the sheath element 26 may be formed from a variety of different materials, including without limitation: a continuous tube or sheet of material; a woven, knitted, or other fabric material; non-woven materials such as a felt; or a composite of two or more different materials. Suitable materials for use as a sheath 26 include tubes or sheets of material that may comprise but are not limited to: polytetrafluoroethylene (PTFE), expanded PTFE, polyester, polyethylene, nylon, rayon, polyimide, polyamide, polypropylene, and/or polyurethane.

The sheath element 26 may be formed from a radially distensible material and/or it may be constructed in a wide variety of configurations. For example, the material may be radially distensible, or radially necking, and/or have a wide range of strength or other properties. Additionally, it may be beneficial to construct the sheath element in the form of a pleated sheath or a helically pleated sheath so as to assist in radial compliance or release of the device.

As is shown in FIG. 1, in one embodiment of the present invention the sheath element 26 is constructed from a continuous tube that is split at its trailing end, at point 37 in FIG. 1, so as to form the first deployment line 34 from the same material as the sheath 26. The deployment line 34 may be formed by, for example, spirally winding, heating, or otherwise manipulating the split tube into thread structure. Further, other materials, such as a thread of polyamide, polyimide, PTFE, ePTFE, polyester or similar material, may be used alone or added to the split tube to provide a more robust deployment line construct.

For deployment of a stent or stent-graft device, a suitable sheath element 26 may comprise a tubular sheath of expanded PTFE with a thickness of approximately 0.0015 to 0.15 mm, a longitudinal tensile strength of approximately 0.5 to 10 kgf. The sheath should have sufficient toughness to withstand any strains that may be applied by the constrained device (e.g., forces from stent apices, fins, anchors, etc.). As is explained below, for some applications it may be desirable for the sheath to have the ability to neck to an intermediate diameter when longitudinal tension is applied to the sheath. The sheath may be formed from any suitable base material, including without limitation a tube, sheet, and/or fibers (e.g., weave or braid of material).

As has been noted, the constraining member 32 serves to provide the effective constraint for the implantable device 20. As such, the constraining member 32 should be formed from a relatively non-compliant material that will resist any expansion force delivered by the implantable device 20. The constraining member 32 may be formed from a variety of different materials, including without limitation: a continuous tube or sheet of material; a woven, knitted, or other fabric material; non-woven materials such as a felt; or a composite of two or more different materials. Additionally, it may be beneficial to construct the constraining member 32 in the form of a pleated sheath or a helically pleated sheath, such as that disclosed in U.S. Pat. No. 8,845,712 to Irwin et al., so as to assist in radial compliance or release of the device. Suitable materials for use as a constraining member 32 include tubes, sheets, or fibers of material that may comprise but are not limited to: polytetrafluoroethylene (PTFE), expanded PTFE, polyester, polyethylene, nylon, rayon, polyimide, polyamide, polypropylene, and/or polyurethane.

The constraining member 32 may be effectively formed from a filamentary material, such that described in U.S. Pat. No. 6,315,792 to Armstrong et al. ("Armstrong et al. Patent"), incorporated in its entity by reference herein. The knitted constraining members described in that patent provide very effective device constraint yet easily unravel from the implantable device during deployment. As has been noted, the Armstrong et al. Patent's constraints have proven to be very accurate and effective in implantable device delivery and deployment. However, by combining the constraining member 32 of Armstrong et al. Patent with the everted sheath element 26 described above, significant benefits have been demonstrated. It has been determined that if the filamentary constraints described in the Armstrong et al. Patent are used alone, the fibers can snag on features of some implantable device constructions (e.g., certain forms of anchors, barbs, stent apices, etc.), which can create difficulties in mounting the constraint during manufacture and/or in releasing the constraint during deployment. By sandwiching the filamentary constraining member construct of the Armstrong et al. Patent within the everted sheath element 26, the sheath element 26 serves to cover and isolate any problematic features on the implantable device 20 so that the constraining member 32 can be readily mounted on the implantable device 20 during manufacture and then readily removed from the implantable device 20 during deployment. This benefit greatly enhances the types of implantable devices that can now be successfully deployed using the apparatus of the Armstrong et al. Patent.

The second deployment line 36 may comprise the same material as the constraining member 26, such as when the constraining member 26 is formed in accordance with certain embodiments of the Armstrong et al. Patent. Alternatively, other materials, such as a thread of polyamide, polyimide, PTFE, ePTFE, polyester or similar material, may be used alone or added to the deployment line 36 to provide a more robust construct.

The process for constructing the deployment apparatus 24 of the present invention is illustrated in FIG. 2 through FIG. 8. FIG. 2 illustrates an implantable device 20, such as a stent or stent-graft, prior to mounting into the deployment apparatus 24 of the present invention. In FIG. 3, the implantable device 20 is placed within sheath element 26.

Figure 4:
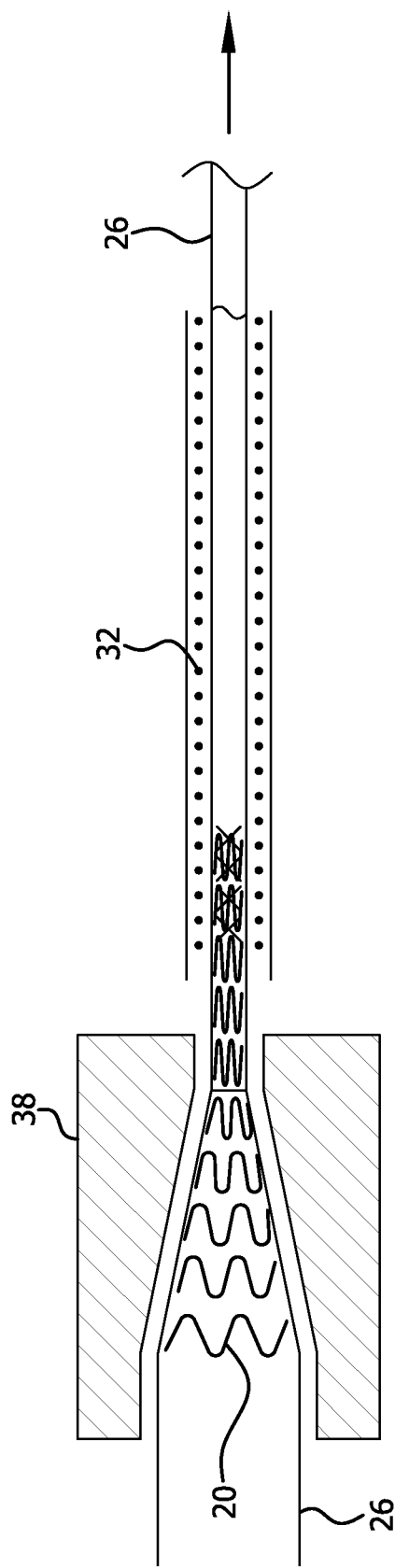
FIG. 4 is a side view, shown partially in cross-section, of the sheath element and implantable device combination illustrated in FIG. 3 being drawn through a funnel into a constraining member.

In FIG. 4 the sheath element 26 and implantable device 20 combination illustrated in FIG. 3 is drawn through a funnel 38 into a constraining member 32. As has been noted, the sheath element 26 is serving as a traction tube to provide a smooth and even surface to help ease the implantable device 20 through the funnel 38 and into the constraining member 32. In this regard, any coating that may be applied to the implantable device 20 is thus protected from abrasion from the funnel 38 and constraining member 32. Additionally, to whatever degree that the sheath element 26 undergoes any necking during the process of pull-down through the funnel 38, the necking force further assists in the compaction of the implantable device 20.

It should be appreciated that the sheath element 26 is also isolating the implantable device 20 from the forces necessary to pull the device 20 through the funnel 38 and into the constraining member 32. In more conventional compaction processes, tether lines would typically be applied to one end of the implantable device 20 in order to pull it through a funnel into a constraint. As such, an implantable device must be constructed from materials and in a manner that allows it to withstand the substantial longitudinal forces necessary to compact it to its delivery dimensions (that is, if the implantable device is not sufficiently robust, it will be damaged under the forces of the tether lines during the compaction process). The compaction forces become significantly greater for longer implantable device constructs and when greater compaction ratios are undertaken. By using the sheath member of the present invention to apply traction forces along the entire length of the implantable device, it is possible to effectively compact implantable devices which would otherwise be too fragile to undergo compaction through conventional traction lines and/or to apply far greater compaction forces (and thus achieve far greater compaction ratios) than would previously be possible. In this regard the sheath element provides augmented axial strength to the implantable device during the compaction and loading processes.

Figure 5:
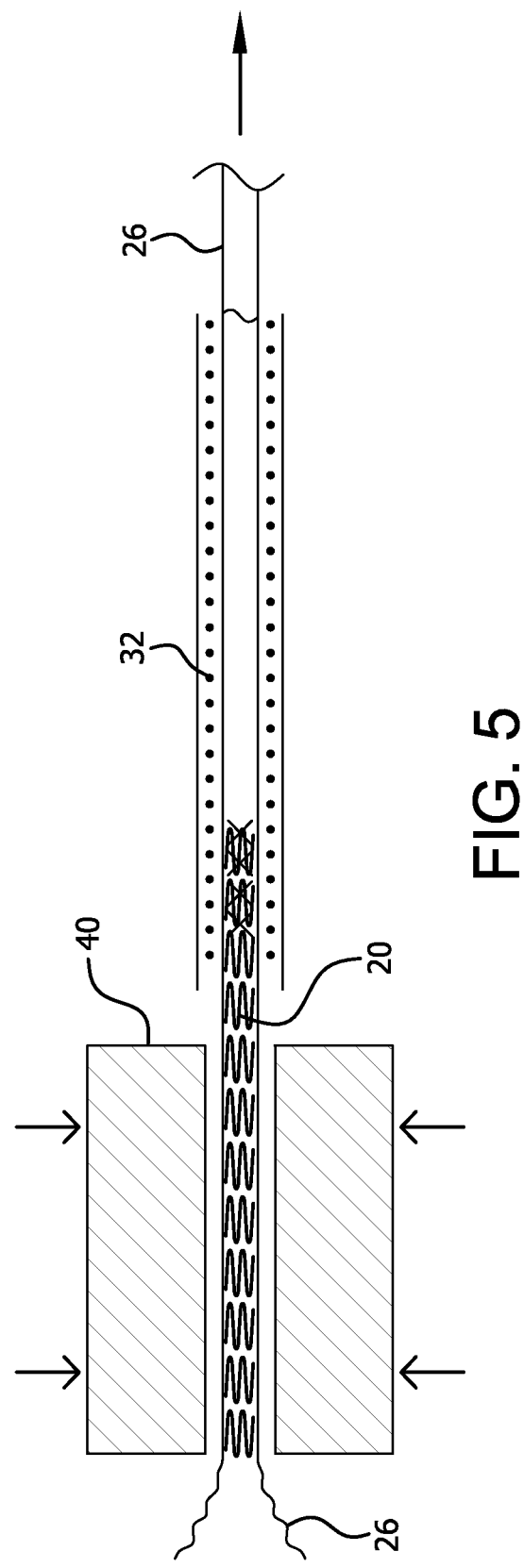
FIG. 5 is a side view, shown partially in cross-section, of the sheath element and implantable device combination illustrated in FIG. 3 being radially compacted and then drawn into a constraining member.

An alternative compaction process is illustrated in FIG. 5. In this embodiment, the sheath element 26 and implantable device 20 combination illustrated in FIG. 3 is compacted by a compression apparatus 40, such as a radial crush device. In this embodiment the sheath element 26 facilitates the compacted implantable device to be more readily pulled out of the compression apparatus and into constraining member 32, with all of the benefits previous noted.

Figure 7:
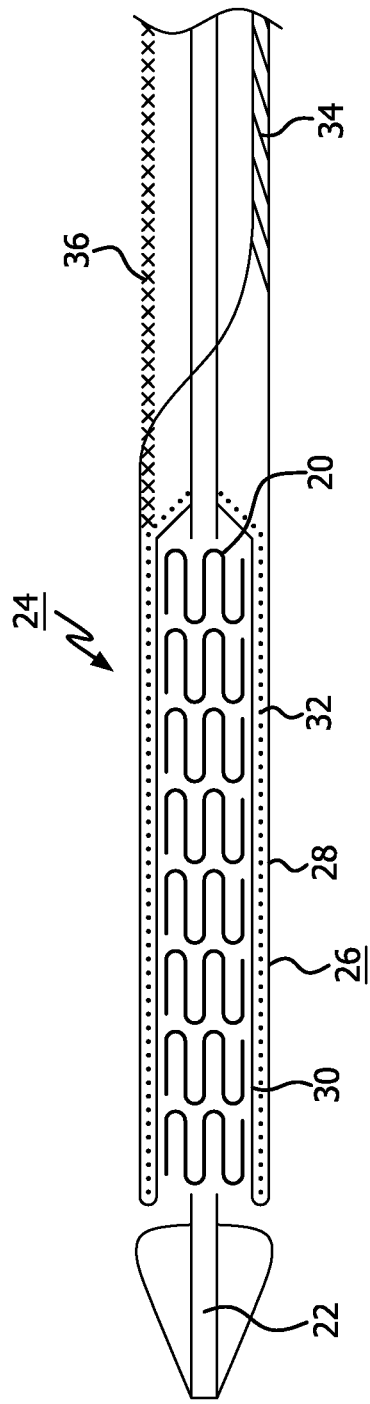
FIG. 7 is a side view, shown partially in cross-section, of the sheath element, implantable device, and constraining member combination illustrated in FIG. 6, shown mounted on a delivery catheter and having traction lines formed to effectuate removal of the sheath element and constraining member during deployment of the implantable device.

Whether compacted by the process illustrated in FIG. 4 or FIG. 5 or through any other suitable means, as is shown in FIG. 6 once the implantable device 20 is compacted into the constraining member 32 there is extra sheath element 26 extending from both sides of the compacted device 20. As is shown in FIG. 7, the constrained device 20 may then be mounted on a delivery catheter 22 and the extra sheath element 26 may then be everted back over the constraining member 32 so as to sandwich the constraining member 32 within the inner layer 30 and outer layer 28 of the sheath element 26. Deployment line 34 may then be attached to or formed out of the sheath element 26. Likewise, deployment line 36 may then be attached to or formed from constraining member 32 (for example, if the constraining member 32 is constructed from a knitted material, such as that described in the Armstrong et al. Patent, the deployment line 36 may comprise an cord formed from the unraveled constraining member 32).

It should be appreciated that for some applications the sheath element 26 may also be employed as a single layer. Among the benefits of employing a single layer sheath element are the opportunity to provide reduced delivery profile and decreased length of deployment line.

Once constructed in the manner described herein, the implantable device 20 and deployment apparatus 24 can be delivered to a desired treatment site in a patient in a conventional manner. It should be appreciated, however, that the encapsulation of the implantable device 20 within the sheath element 26 provides additional protection to the implantable device 20 during the delivery process. As has been noted, when an implantable device 20 is provided with a drug or other bioactive coating, it is desirable that the coating is not exposed prior to reaching the intended deployment site. With certain constraint constructs, such as open mesh or open filament braids and the like, drug coatings will necessarily be exposed to blood and tissue long before reaching the intended deployment site, which can lead to possible abrasion of the coating from the device and unintended release of the bioactive materials in undesirable locations in the body. However, through use of the sheath member 26 of the present invention, the bioactive coating can be safeguarded against damage or premature release independent of how open the structure of the constraining devices may be.

Figure 8:
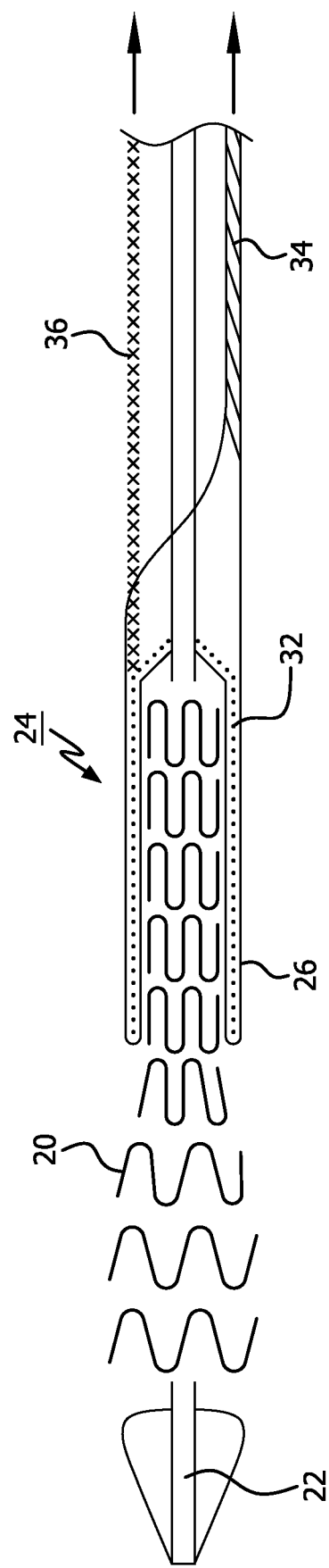
FIG. 8 is a side view, shown partially in cross-section, of the implantable device and delivery apparatus shown in FIG. 7, with the implantable device shown partially deployed.

Once the constrained device 20 is properly positioned in the body, the device 20 can be released by actuating the two deployment lines 34 and 36, with each of the constraining member 32 and the sheath element 26 pulling away from the device upon actuation. This process is illustrated in FIG. 8, with implantable device 20 shown beginning to deploy from the deployment apparatus 24.

While there are many noted benefits in providing a deployment apparatus that includes both a sheath element and a constraining member, it has been determined that there is one challenge when trying to remove two covers simultaneously from the constrained implantable device. Since the sheath element 26 and the constraining member 32 may be constructed of different materials and comprise different forms, they are unlikely to retract at the same rate or in the same manner. Additionally, depending on construction, the deployment lines may not actuate at linear rates, thus requiring some degree of modulation of the rate of actuation of each of the lines. This presents the clinician with an undesirable challenge of trying to actuate the two deployment lines 34 and 36 simultaneously but at different rates.

The present inventors have determined that this challenge can be fully addressed by employing one of a variety of differential mechanisms that allow the clinician to apply a single deployment force to the deployment apparatus 24 while the differential mechanism automatically modulates the rate of actuation of each of the deployment lines 34 and 36.

Figure 9:
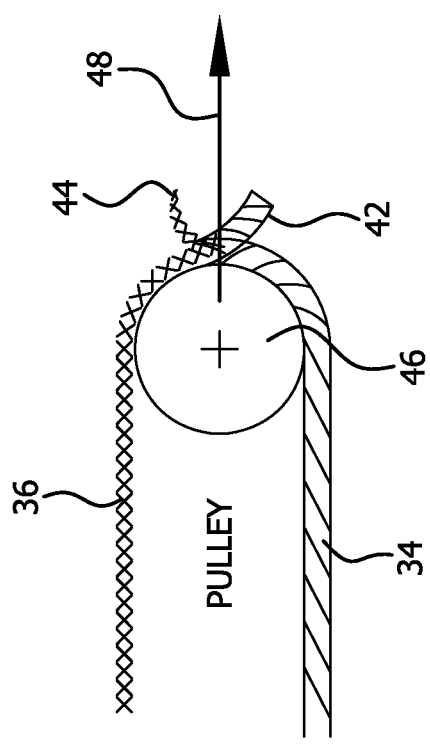
FIG. 9 through FIG. 12 are schematic representations of various apparatus that may be used to effectuate simultaneous removal of multiple traction lines that may be employed with the present invention.

FIG. 9 through FIG. 12 illustrate various apparatus that may be used to effectuate simultaneous removal of multiple traction lines that may be employed with the present invention. FIG. 9 illustrates the simplest form of differential whereby a the two deployment lines 34 and 36 are attached together at their terminal ends 42 and 44, respectively, and a pulley 46 is employed so that varying retraction rates on each of the deployment lines 34, 36 are instantly accommodated. The clinician simply applies a single deployment force 48 to the pulley and the sheath element and constraining member will retract at the same rate while any rate differential between the two are corrected by the pulley 46.

Figure 10:
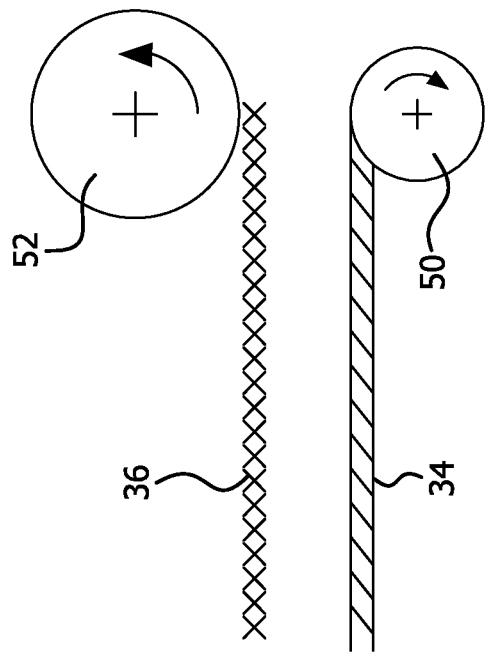

FIG. 10 illustrates another form of differential whereby any difference in rate of withdrawal is pre-calculated and different fixed ratio pulleys 50, 52 are used to withdraw each of the deployment lines 34, 36 at their predetermined rates.

Figure 11:
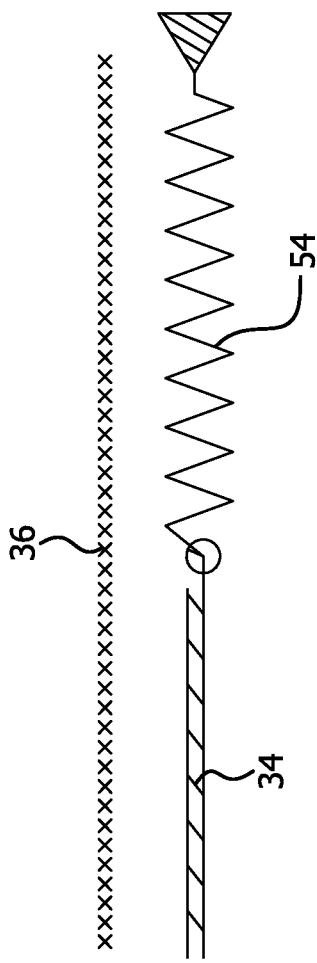

FIG. 11 illustrates still another form of differential whereby a spring or other passive displacement mechanism 54 is associated with the deployment line 34 that is determined to require the most slack during deployment (that is, the deployment line that needs to be withdrawn slower). In this manner, the clinician can pull both lines at an even rate but the lines will effectively withdraw at their appropriate differential rates.

Figure 12:
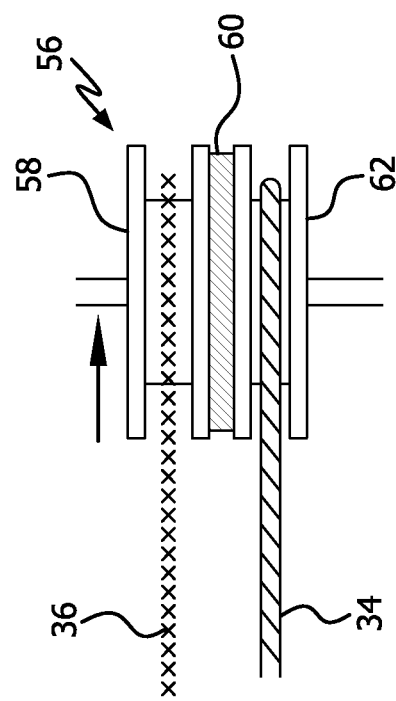

FIG. 12 illustrates yet another form of differential whereby a clutch drive 56 is employed so that a driven pulley 58 takes up one of the deployment lines 36 at a set rate and a friction interface 60 between the driven pulley 58 and a second pulley 62 provides a clutch mechanism so that deployment line 34 will accumulate at a slower rate of speed.

Figure 13:
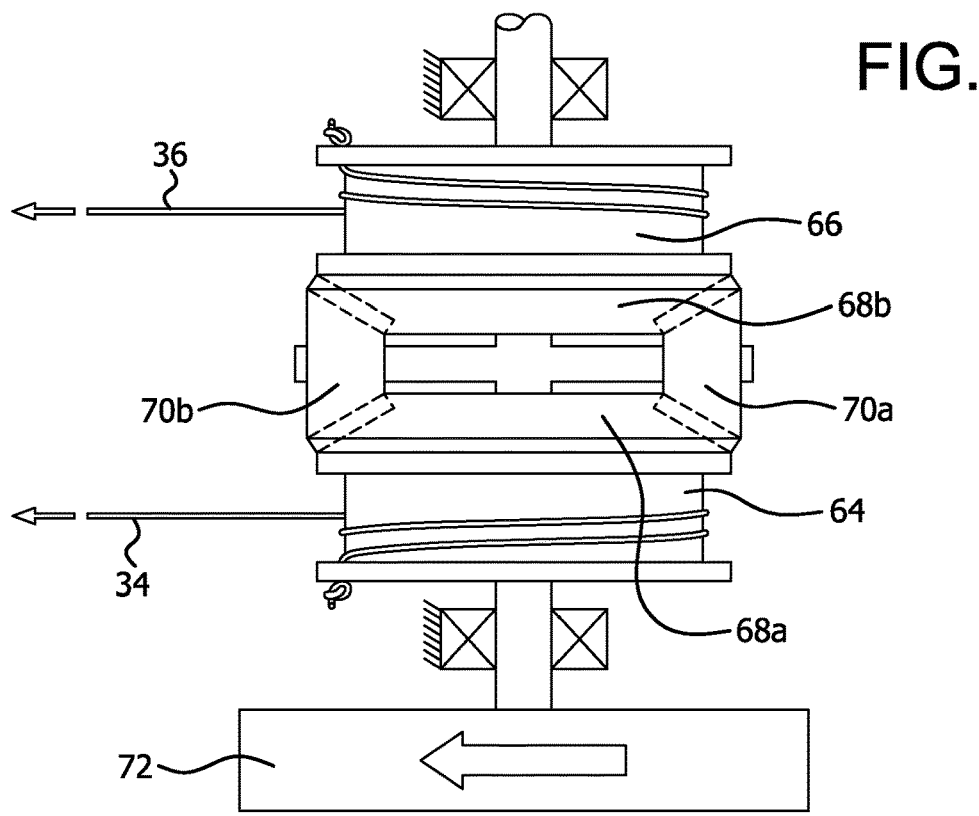
FIG. 13 is a top plan view, shown partially in cross-section, of a differential gear that may be used to effectuate simultaneous removal of multiple traction lines that may be employed with the present invention.

A more sophisticated differential mechanism is illustrated in FIG. 13. In this embodiment, two pulleys 64, 66 are provided, each associated with deployment lines 34, 36, respectively. Pulley bevel gears 68a, 68b and planetary bevel gears 70a, 70b are mounted between the two pulleys 64, 66 so as to accommodate different rates of actuation of each of the pulleys 64, 66. A clinician-actuated thumb wheel 72 is provided to actuate the planetary gears through a center shaft with thumb wheel fixed at one end, and similarly to the clutch mechanism illustrated in FIG. 12, the planetary gears 70a, 70b serve to accommodate different actuation rates between the two pulleys 64, 66. The bevel gears may be chosen to actuate each of the pulleys at their appropriate rates. For example, the sum of rotation of pulleys 64 and 66 can be established to be, for instance, 2× the input rotation of the thumb wheel 72.

Figure 14:
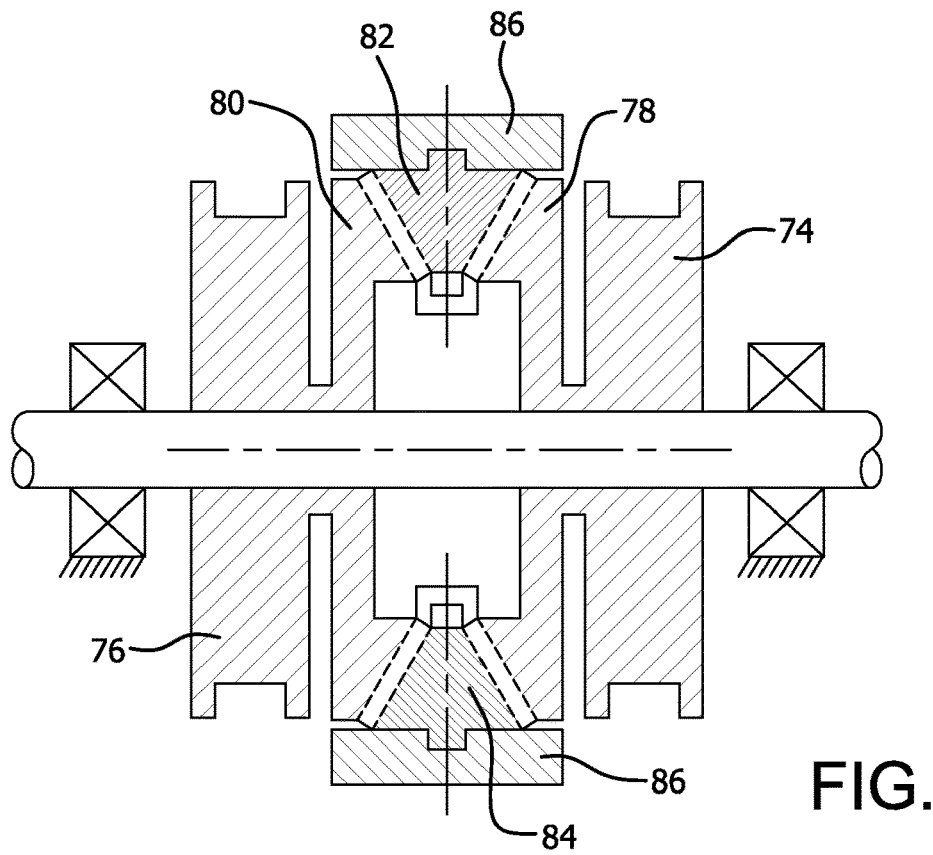
FIG. 14 is a cross-section view of another embodiment of a differential gear that may be used to effectuate simultaneous removal of multiple traction lines that may be employed with the present invention.

A similar differential mechanism is illustrated in FIG. 14. In this embodiment, pulleys 74 and 76 are each associated with each of the deployment lines (not shown) and are attached, respectively, to ring gears 78, 80. Planetary gears 82, 84 are each provided with a clinician-actuated thumb wheel 86 that engages directly with the planetary gears.

It should be understood that the various differential mechanisms described herein are by way of illustration only and that any of these or other mechanism may be employed within the scope of the present invention. Further various improvements or refinements to these mechanism are also within the scope of the present invention, including, for example, that a motor or other drive mechanism may be substituted for thumb wheels in the embodiments of FIG. 13 and FIG. 14.

For some applications, it may be beneficial to transfer the implantable device to an intermediate compacted diameter prior to final compaction and mounting of the implantable device for delivery. For example, by compacting the implantable device in multiple steps, a thinner and less robust sheath may be used for final device compaction and delivery, which may allow for desirable smaller device delivery dimensions. One method of accomplishing is to modify the mounting procedure illustrated in FIGS. 2 to 6, above, with additional process steps as illustrated in FIGS. 15 to 18.

Figure 15:
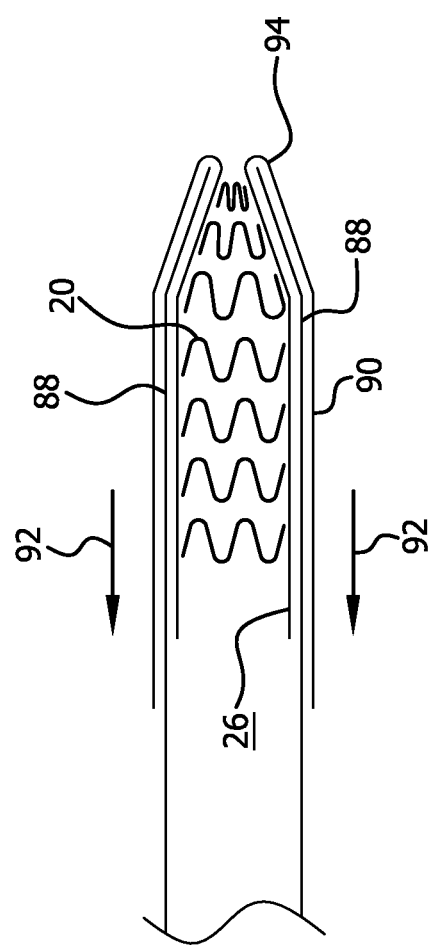
FIG. 15 is a side view, shown partially in cross-section, of the sheath element and implantable device combination illustrated in FIG. 3 being drawn into a transfer funnel, with a portion of the sheath element everted over the transfer funnel.

In FIG. 15 the sheath element 26 and implantable device 20 combination illustrated in FIG. 3 is drawn into a transfer funnel 88, with a segment 90 of the sheath element 26 everted over the transfer funnel 88. The compaction of the implantable device 20 into the transfer funnel 88 may be accomplished by applying tension 92 to the segment 90 so as to draw the sheath 26 and device 20 into the funnel 88. Once the implantable device 20 is positioned at the tip 94 of the transfer funnel 80, the device is ready for transfer.

Figure 16:
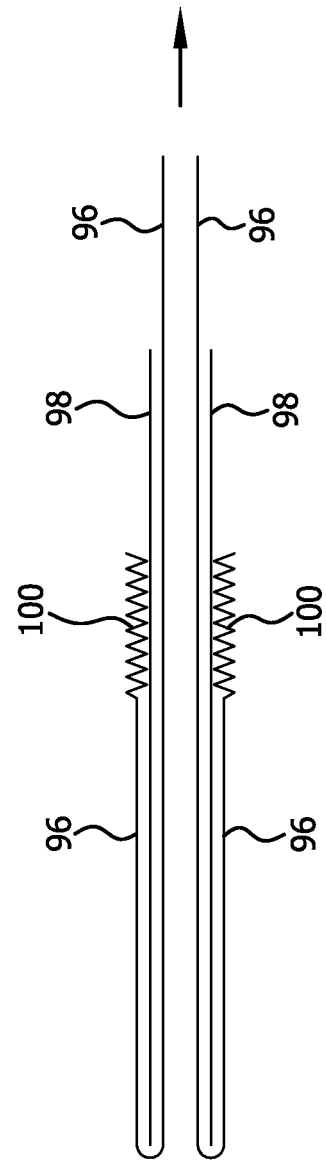
FIG. 16 is a cross-section side view of a second sheath element everted over a transfer tube.

FIG. 16 shows a second sheath element 96 that is everted over a transfer tube 98. The second sheath element 96 is configured to be a diameter smaller than the diameter of sheath element 26. The transfer tube 98 is constructed from an essentially non-compliant material, such as a metal or plastic hypotube. The transfer tube 98 has a diameter that is approximately equal to that of the tip 94 of the transfer funnel 88. A portion 100 of the second sheath on the outside of the transfer tube 98 may be compacted or "scrunched" to make actuation of the second sheath easier in the transfer step described below.

In order to accomplish transfer of the implantable device 20 from the sheath element 26 to the second sheath element 98, the implantable device 20, sheath element 26, and transfer funnel 88 combination shown in FIG. 15 is placed in abutted orientation with the second sheath element 96 and transfer tube 98 combination shown in FIG. 16, as is shown in FIG. 17. By applying tension 92 to the sheath element 26 and simultaneously applying tension 102 to the second sheath element 98, as shown in FIG. 17, the implantable device 20 will transfer from the transfer funnel 88 and sheath element 26 into the transfer tube 98 and second sheath element 96. This transfer is shown partially completed in FIG. 17.

Once the implantable device 20 is fully transferred into the second sheath element 96, the device 20 and second sheath 98 can be removed from the transfer tube, as is shown in FIG. 18. The implantable device 20 is now contained at a small diameter and/or contained in a sheath with thinner wall thickness than the device and sheath illustrated in FIG. 3. At this stage the combined device and sheath can be further processed as previously described with respect to FIG. 4 through 6.

It should be appreciated from this description of FIGS. 15 to 18 that the present invention may be practiced through a number of ways whereby the implantable device may be partially compacted to one or more intermediate diameters during the manufacturing process.

As has been explained, the present invention provides many benefits over prior medical device deployment apparatus, including without limitation:

(1) The present invention provides a delivery system that protects medical device during delivery in a body while providing simple, accurate, and reliable device deployment that is scalable to work on a wide variety of implantable device forms and sizes.

(2) The delivery system is configured so that loading and deployment forces are not directly related to device diameter, length, or design, thus allowing a more universal delivery system across various delivered device configurations and product lines. In this regard, forces required to constrain implantable devices and deploy implantable devices can be decoupled from the length and other properties of the implantable devices.

(3) By employing the sheath element to present a more consistent surface on the outside of the implantable device, deployment forces may be smoother during delivery so as to minimize catheter movement (for example, increases in delivery force due to adverse interaction between the implantable device and the constraint can be avoided). Similarly, the present invention can accommodate deployment of devices with irregular features (e.g., scallops, barbs, anchors, apices, and other features that may otherwise interfere with smooth operation of deployment apparatus).

(4) The use of the sheath element may help reduce device delivery profiles, both by allowing compaction forces to be decoupled from device longitudinal tensile strength and by providing a smoother and possibly more lubricious surface on the outside of the implantable device to allow for easier compaction of the device. By eliminating direct tensioning of device during loading, the present invention also allows for lower implantable device mass and lower profile.

(5) The present invention can be configured so as to contain delivery lines within a sheath element in order to reduce or eliminate "bow-stringing" of the line during deployment.

(6) By encapsulating the implantable device prior to loading and keeping it encapsulate until deployment, the present invention imparts minimal stress to the implantable device. For drug delivery devices, this can reduce drug loss and particulation during handling of the device in both manufacture and use. In this regard, the encapsulation of the device can reduce or eliminate contact between device and tooling during device loading and mounting and also may isolate the device from surface shear and other damage during delivery and deployment.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A medical device deployment system comprising:
an expandable medical device having first and second ends and having a larger deployed diameter, and a smaller compacted diameter in a delivery configuration adapted for advancement through a vasculature of a patient;
a sheath surrounding the expandable medical device in the delivery configuration, said sheath everted back over itself, wherein an outer portion of said sheath surrounds an inner portion of said sheath, the sheath being split at a trailing end to form a deployment line;
a filamentary constraining member positioned between the inner and outer portions of the sheath in the delivery configuration such that the outer portion of the sheath surrounds the constraining member from the first end to at least the second end of the expandable medical device, and the filamentary constraining member including a cord configured to be tensioned to unravel the constraining member, wherein the expandable medical device is deployed to the larger deployed diameter by application of simultaneous actuation forces to the sheath and the cord of the filamentary constraining member.

2. The deployment system of claim 1 wherein the expandable medical device is self-expanding.

3. The deployment system of claim 1, wherein the sheath is tubular and the outer portion of the sheath coaxially surrounds the inner portion of the sheath.

4. The deployment system of claim 1 wherein said simultaneous actuation forces cause withdrawal of the sheath and the constraining member at two different rates.

5. The deployment system of claim 4, wherein said two different rates comprise varying differential rates.

6. The deployment system of claim 1 wherein the expandable medical device includes a bio-active coating and the sheath acts to protect the coating during handling of the device.

7. The deployment system of claim 6 wherein the bio-active coating comprises a drug coating.

8. The deployment system of claim 1 wherein the sheath comprises a helically pleated sheath.

9. The deployment system of claim 1 wherein the sheath is operable to provide augmented axial strength to the expandable medical device.

10. The deployment system of claim 1 wherein interaction of the sheath and constraining member during application of the simultaneous actuation forces to the sheath and the filamentary constraining member serve to decouple said simultaneous actuation forces from the expandable medical device.

11. The deployment system of claim 1 wherein the constraining member unravels upon the application of said simultaneous actuation forces.

12. The deployment system of claim 1 wherein the sheath comprises a filament that unravels upon the application of the simultaneous actuation forces.

13. A medical device deployment system comprising:
an expandable medical device having first and second ends and having a larger deployed diameter, and a smaller compacted diameter in a delivery configuration adapted for advancement through a vasculature of a patient;
a first sheath surrounding the expandable medical device at the smaller compacted diameter, said sheath everted back over itself, wherein an outer portion of said first sheath surrounds an inner portion of said first sheath, the first sheath being split at a trailing end to form a deployment line;
a second sheath being located between the inner and outer portions of the first sheath such that the outer portion of the first sheath surrounds the second sheath from the first end to at least the second end of the expandable medical device, wherein the first sheath and the second sheath are removed by application of two separate tensile forces to the first sheath and the second sheath.

14. The deployment system of claim 13 wherein the expandable medical device is self-expanding.

15. The deployment system of claim 13 wherein the outer portion of the first sheath coaxially surrounds the inner portion of the first sheath.

16. The deployment system of claim 13 wherein said two separate tensile forces cause withdrawal of the first sheath and second sheath at two different rates.

17. The deployment system of claim 16 wherein said two different rates comprise varying differential rates.

18. The deployment system of claim 13 wherein the expandable medical device includes a bio-active coating and the first sheath acts to protect the coating during delivery of the device.

19. The deployment system of claim 18 wherein the bio-active coating comprises a drug coating.

20. The deployment system of claim 13 wherein the first sheath comprises a helically pleated sheath.

21. The deployment system of claim 13 wherein the first sheath is operable to provide augmented axial strength to the expandable medical device.

22. The deployment system of claim 13 wherein interaction of the first sheath and the second sheath during application of simultaneous actuation forces to the first sheath and the second sheath serve to decouple said simultaneous actuation forces from the expandable medical device.

23. The deployment system of claim 13 wherein the second sheath comprises a filament that unravels upon the application of the tensile force.

24. The deployment system of claim 13 wherein the first sheath comprises a filament that unravels upon the application of the tensile force.

25. A medical device deployment system comprising:
a first sheath having a first deployment line and a second sheath having a second deployment line, the first sheath being split at a trailing end to form the first deployment line, the second sheath being located between inner and outer portions of the first sheath such that the outer portion of the first sheath completely surrounds the second sheath in a delivery configuration adapted for advancement through a vasculature of a patient, the first sheath being configured to evert upon tensioning the first deployment line, wherein each of said first and second sheaths is non-proportionally actuated by an application of tension to the first and second deployment lines of the first and second sheaths in response to an application of a single input force, said single input force being variably distributed between the first and second deployment lines of the first and second sheaths.

26. The deployment system of claim 25 wherein said single input force is variably distributed between the first and second deployment lines of the first and second sheaths through use of a pulley.

27. The deployment system of claim 25 wherein the single input force is variably distributed between the first and second deployment lines of the first and second sheaths through use of a differential element.

28. The deployment system of claim 25 wherein the single input force is variably distributed between the first and second deployment lines of the first and second sheaths through use of a clutch mechanism.

* * * * *